US00PP35956P2

(12) United States Plant Patent
de Silva

(10) Patent No.: US PP35,956 P2
(45) Date of Patent: Jul. 2, 2024

(54) ***POGONATHERUM* PLANT NAMED 'ORPOCEY'**

(50) Latin Name: *Pogonatherum paniceum*
Varietal Denomination: ORPOCEY

(71) Applicant: Ornamentex B.V., 's-Gravenzande (NL)

(72) Inventor: Dilip de Silva, Boralesgamuwa (LK)

(73) Assignee: Ornamentex B.V., 's-Gravenzande (NL)

( * ) Notice: Subject to any disclaimer, the term of this patent is extended or adjusted under 35 U.S.C. 154(b) by 0 days.

(21) Appl. No.: 18/445,658

(22) Filed: Dec. 12, 2023

(51) Int. Cl.
*A01H 5/00* (2018.01)
*A01H 6/00* (2018.01)

(52) U.S. Cl.
USPC ..... Plt./384
CPC ..... *A01H 6/00* (2018.05)

(58) Field of Classification Search
USPC ..... Plt./384
CPC ..... A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Pogonatherum paniceum* plant named 'ORPOCEY' which is characterized by a very compact and densely-foliaged growth habit, broadly lanceolate foliage borne on short aerial stems, vibrant dark green and glossy foliage, a fast growth rate, as well as the stability of these characteristics from generation to generation.

3 Drawing Sheets

Latin name of the genus and species: The Latin name of the genus and species of the novel variety disclosed herein is *Pogonatherum paniceum.*

Variety denomination: The inventive variety of *Pogonatherum* disclosed herein has been given the variety denomination 'ORPOCEY'.

BACKGROUND OF THE INVENTION

Parentage: The new plant originated as a spontaneous, whole-plant mutation. The mutation was discovered at a greenhouse in North Central Province, Sri Lanka, in 2018. Said mutation was discovered growing amongst a plurality of cultivated, unnamed *Pogonatherum paniceum* plants (not patented). The mutation exhibited a fast growth rate, freely-branched and densely-foliaged growth habit relative to the parent. The mutation was isolated and grown to a mature size in order to evaluate stability and uniqueness of the characteristics first observed. Upon confirmation of the stability and uniqueness, the new plant was selected for commercialization and given the name, 'ORPOCEY'.

Asexual Reproduction: Asexual reproduction of the new cultivar 'ORPOCEY', by way of meristematic tissue culture, was first initiated in June of 2018 in Boralesgamuwa, Sri Lanka. Through eight generations of asexual reproduction, the unique features of this cultivar have proven to be stable and true to type.

SUMMARY OF THE INVENTION

The cultivar 'ORPOCEY' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ORPOCEY'. These characteristics in combination distinguish 'ORPOCEY' as a new and distinct *Pogonatherum* cultivar:

1. *Pogonatherum* 'ORPOCEY' exhibits a very compact, densely-foliaged growth habit; and
2. *Pogonatherum* 'ORPOCEY' exhibits broadly lanceolate foliage borne on short aerial stems; and
3. *Pogonatherum* 'ORPOCEY' exhibits vibrant dark green, glossy foliage; and
4. *Pogonatherum* 'ORPOCEY' exhibits a fast growth rate.

BOTANICAL DESCRIPTION OF THE PLANT

Figure 1:
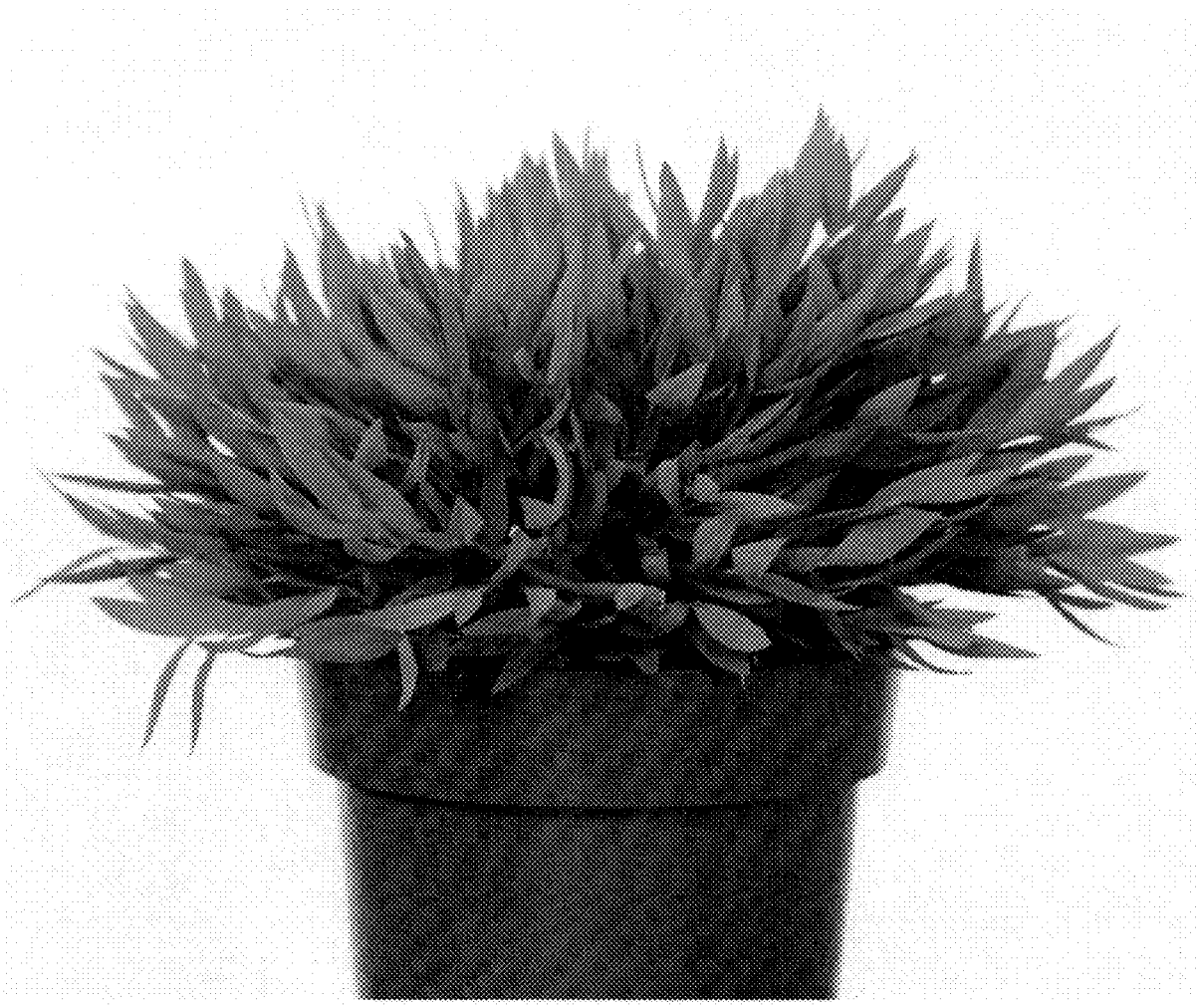
FIG. 1 illustrates, as nearly true as it is reasonably possible to make the same in color photographs of this type, an exemplary 12-month-old 'ORPOCEY' plant in a 12 cm nursery pot, grown in a greenhouse in Honselersdijk, The Netherlands.
Figure 2:
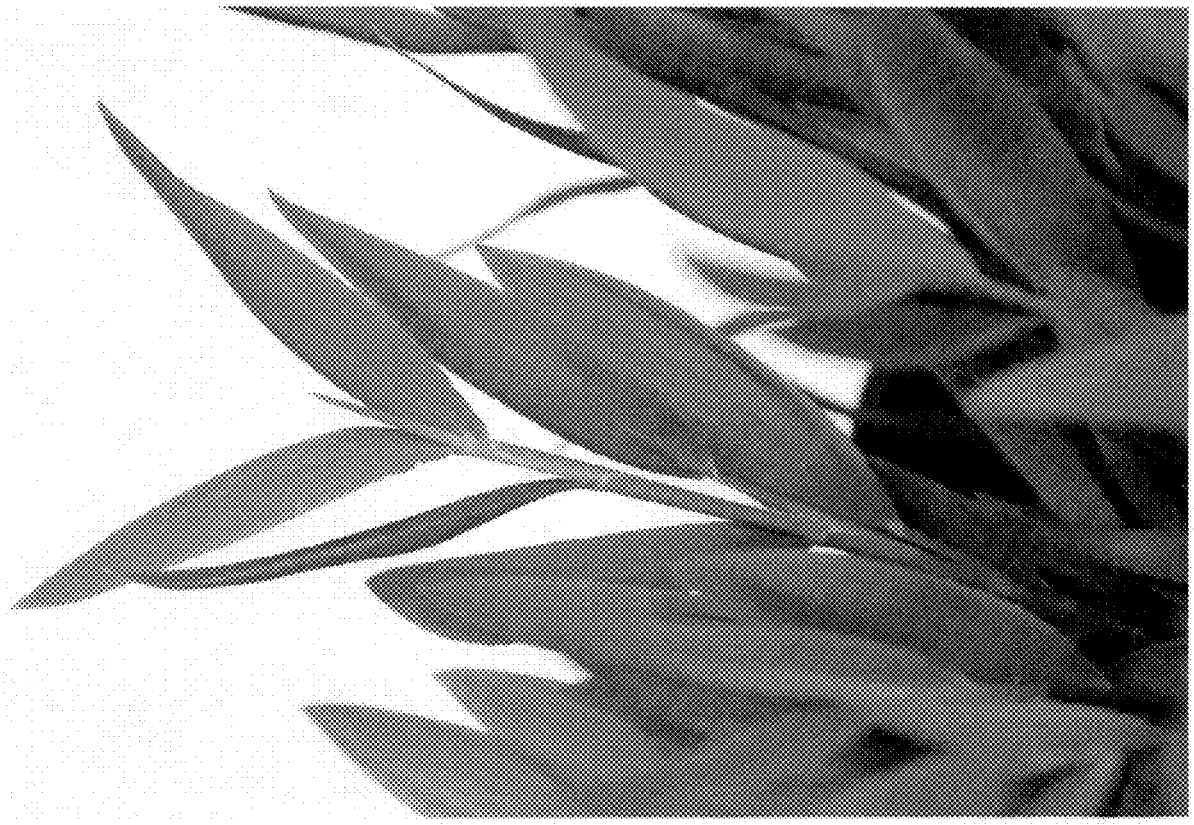
FIG. 2 illustrates, as nearly true as it is reasonably possible to make the same in color photographs of this type, the mature foliage of 'ORPOCEY'.
Figure 3:
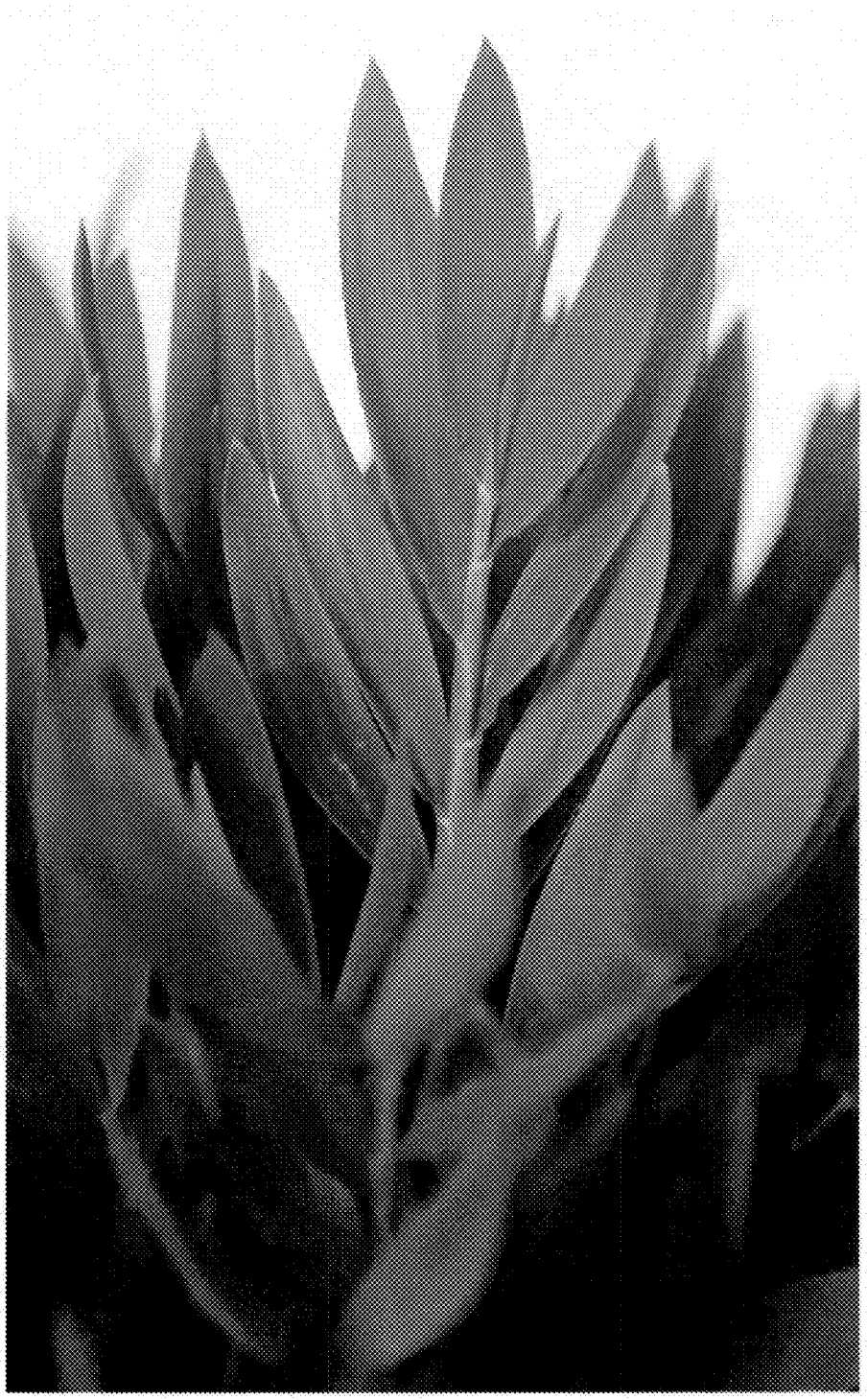
FIG. 3 illustrates, as nearly true as it is reasonably possible to make the same in color photographs of this type, the lateral branch of 'ORPOCEY'.

The following observations and measurements were made in March of 2023 and describes a 12-month-old 'ORPOCEY' plant grown in a 12 cm nursery pot grown in a greenhouse in North Central Province, Sri Lanka. Plants were grown using conventional greenhouse production protocols for *Pogonatherum* which consisted of growing under 50 percent shade, watering with regular overhead irrigation and ebb-and-flood benches, and slow-release fertilizer applications as needed. No pest or disease control measures were utilized in production and no photoperiodic treatments or artificial light was given to the plants.

Those skilled in the art will appreciate that certain characteristics will vary with older or, conversely, with younger plants. 'ORPOCEY' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, 2015 (sixth edition).

A botanical description of 'ORPOCEY' and comparisons with the parent and most similar commercial variety of *Pogonatherum* are provided below.

Plant description:

*Growth habit*.—Perennial ornamental grass; tightly-clumping, bushy habit with foliage borne on aerial stems; broad-spreading to upright.

*Plant profile*.—Flattened globular.

*Average height from base to top of foliage*.—12.9 cm.

*Average width*.—24.7 cm.

*Growth rate*.—Moderately fast growing.

*Plant vigor*.—Moderately to highly vigorous.

*Propagation method*.—Meristematic tissue culture micropropagation; approximately 16 weeks, at an ambient average temperature of 23 to 24 degrees Celsius, are required to produce a rooted plantlet that is ready for planting.

*Time to produce a finished plant*.—Approximately 12 weeks are required to produce a fully rooted and marketable 10 cm plant when grown under greenhouse conditions.

*Disease and pest resistance or susceptibility*.—Plants have not been observed to be susceptible or resistant to pathogens and pests common to *Pogonatherum* spp.

*Environmental tolerances*.—Adapt to at least USDA Zones 10 and 13; moderate tolerance to rain; moderate to high tolerance to wind; low tolerance to drought.

Root system:

*General*.—Moderately dense network of fibrous roots.

*Distribution in the soil profile*.—Roots are relatively deep.

*Texture*.—Fibrous, with root hairs present.

Stem:

*Branching habit*.—Freely branching with an abundance of main stems, each bearing lateral branches.

*Number of main stems per plant*.—80.

*Number of lateral branches per plant*.—150.

*Aspect*.—Rounded.

*Length of main stems*.—8.2 cm.

*Diameter of main stems*.—0.1 cm.

*Internode length on main stems*.—1.2 cm.

*Attitude*.—The attitude of the main stems ranges from 10 to 90 degrees from horizontal; 50 degrees on average.

*Strength*.—Strong.

*Texture and luster*.—Glabrous and moderately glossy.

*Color, juvenile*.—Yellow-green, nearest to RHS N144D.

*Color, mature*.—Yellow-green, nearest to a mixture of RHS 146C and 152D.

*Color at internodes*.—Yellow-green, nearest to a mixture of RHS 146C and 152D.

Foliage:

*Arrangement*.—Alternate; distichous.

*Division*.—Simple.

*Attachment*.—Sheathed.

*Quantity*.—Average of 7 leaves per lateral branch.

*Lamina*.—Dimensions — 3.2 cm long and 0.8 cm wide, on average. Shape — Broadly lanceolate. Aspect — Concave. Apex — Acute. Base — Cuneate; sheathed. Sheath — Length — 1.6 cm. Width — 0.1 cm. Texture — Smooth and glabrous. Luster — Slightly glossy. Margins — Entire and ciliate. Hairs are very short and silky, with an average length of 0.5 mm, and colored white, nearest to RHS N155A. Color — Green, nearest to RHS 143C, and veined darker, nearest to RHS 137A. Margin — Entire; occasionally finely-undulated. Pubescence, texture and luster of adaxial surface — Glabrous, smooth, and slightly to moderately glossy. Pubescence, texture and luster of abaxial surface — Glabrous, smooth, and slightly glossy. Color — Juvenile foliage, adaxial surface — Green, nearest to in between RHS 143A and 143B. Juvenile foliage, abaxial surface — Green, nearest to RHS 138A. Mature foliage, adaxial surface — Green, nearest to RHS 137A. Mature foliage, abaxial surface — Green, nearest to RHS 137B. Venation — Pattern — Parallel. Venation color, adaxial surface — Green, nearest to RHS 137A. Venation color, abaxial surface — Green, nearest to RHS 138A.

*Ligules*.—Length — 0.1 mm. Texture — Membranous Margins — Entire and ciliate. Hairs are very short and silky, with an average length of 0.5 mm, and colored white, nearest to RHS N155A. Luster — Matte. Color — Green-white, nearest to RHS 143C.

Inflorescence: No flowering has been observed to date.

Bud: No flowering has been observed to date.

Flower: No flowering has been observed to date.

Reproductive organs: No flowering has been observed to date.

Seed and fruit: No flowering has been observed to date.

COMPARISONS WITH THE PARENT PLANT

Plants of the new cultivar 'ORPOCEY' differ from the parent, an unnamed *Pogonatherum paniceum* plant (not patented), by the characteristics described in Table 1.

TABLE 1

| Characteristic | 'ORPOCEY' | The parent. |
|---|---|---|
| Growth habit. | More compact than the parent. | Less compact, relative to 'ORPOCEY'. |
| Length of main stem internodes. | Shorter than the parent. | Longer than 'ORPOCEY'. |

TABLE 1-continued

| Characteristic | 'ORPOCEY' | The parent. |
|---|---|---|
| General coloration of the foliage. | Darker green, relative to the parent. | Lighter green, relative to 'ORPOCEY'. |
| Foliage luster. | Glossier than the parent. | Less glossy, relative to 'ORPOCEY'. |

COMPARISON WITH THE MOST SIMILAR CULTIVAR KNOWN TO THE INVENTOR

Plants of the new cultivar 'ORPOCEY' differ from the commercial variety, *Pogonatherum* 'Monica' (not patented), in the following characteristics described in Table 2 below.

TABLE 2

| Characteristic | 'ORPOCEY' | 'Monica' |
|---|---|---|
| Growth habit. | Bushier than 'Monica'. | Less bushy than 'ORPOCEY'. |
| Rate of growth. | Faster-growing than 'Monica'. | Slower-growing than 'ORPOCEY'. |
| Foliage shape. | Broadly lanceolate. | Narrowly lanceolate. |

That which is claimed is:

1. A new and distinct *Pogonatherum paniceum* plant named 'ORPOCEY', substantially as described and illustrated herein.

* * * * *